United States Patent [19]

Schroer

[11] 3,957,994

[45] May 18, 1976

[54] TOPICAL ANTI-INFLAMMATORY COMPOSITION AND METHOD OF USE

[75] Inventor: Richard Allen Schroer, Silverado, Calif.

[73] Assignee: Nelson Research & Development Company, Irvine, Calif.

[22] Filed: Dec. 19, 1974

[21] Appl. No.: 534,228

[52] U.S. Cl. ............................................. 424/253
[51] Int. Cl.² ...................................... A61K 31/52
[58] Field of Search ................................... 424/253

[56] References Cited
UNITED STATES PATENTS 3,457,263   7/1969   Regnier et al. .................... 424/253
3,472,931   10/1969  Stoughton .......................... 424/253

OTHER PUBLICATIONS

Chem. Abst. Vol. 66 — 74599m, (1967).
Chem. Abst. Vol. 68 — 16136p, (1968).
Chem. Abst. Vol. 73 — 102083d, (1970).

*Primary Examiner*—Stanley J. Friedman
*Attorney, Agent, or Firm*—Martin A. Voet

[57] ABSTRACT

There is disclosed a novel topical anti-inflammatory composition comprising theophylline and 2-pyrrolidone or an N-lower alkyl-2-pyrrolidone.

10 Claims, No Drawings

TOPICAL ANTI-INFLAMMATORY COMPOSITION AND METHOD OF USE

BACKGROUND OF THE INVENTION

1. Field of the Invention

The invention relates generally to novel anti-inflammatory compositions. More particularly, the present invention relates to novel topical anti-inflammatory compositions useful in temporarily alleviating the symptoms of inflammation in humans and animals.

2. Background of the Prior Art

Theophylline is a xanthine compound which has heretofore been used therapeutically as a smooth muscle relaxant. It is typically administered systemically by oral or intravenous or intramuscular injection.

SUMMARY OF THE INVENTION

It has now been unexpectedly discovered that the novel compositions of the present invention, utilizing theophylline as an active ingredient, provide effective, therapeutically useful topical anti-inflammatory activity.

The invention described herein generally relates to novel topical anti-inflammatory compositions comprising about 0.1 to about 1% theophylline and about 5 to about 99% of 2-pyrrolidone or an N-lower alkyl-2-pyrrolidone, and their method of use in the treatment of inflammation, i.e. in the temporary alleviation of the signs and symptoms of inflammation.

The amount of theophylline to be used in the present invention is that amount of theophylline which is effective therapeutically in the temporary alleviation of the signs and symptoms of inflammation. Typical therapeutic amounts are somewhat dependent on the type and severity of the inflammation and its location, but these amounts generally range from about 0.1 to about 1% and preferably about 0.3 percent by weight of the composition. Theophylline may be dissolved in a vehicle of this invention and topically applied to affected areas of the skin in any convenient form, e.g. cream, lotion, spray, solution, etc.

2-Pyrrolidone and N-lower alkyl-2-pyrrolidones are available commercially and are made by a number of methods known to those of skill in the art as exemplified by U.S. Pat. Nos. 2,555,353 and 2,267,757. N-lower alkyl-2-pyrrolidones include the straight and branch chain lower alkyl groups having 1–4 carbon atoms. N-methyl-2-pyrrolidone is preferred.

The amount of 2-pyrrolidone or N-lower alkyl-2-pyrrolidone which may be used in the present invention ranges from about 5 to about 99.9 percent and preferably about 10 to about 50 percent and especially about 20 percent by weight of the composition.

An effective amount of the composition, as the term is used herein, refers to that amount of composition which is effective therapeutically in the treatment of inflammation. Typical inflammations in which the present compositions are useful include conventional inflammations, such as, for example, contact dermatitis, eczema, psoriasis, sunburn, etc. The composition is generally applied about one to three times daily in conventional amounts, that is, amounts sufficient to thinly spread over the affected areas. The treatment is continued until or sometime after all of the manifestations of the inflammation have disappeared.

Ingredients which may be used in these formulations include conventional formulating ingredients, such as, for example, Freons, ethyl alcohol, isopropyl alcohol, acetone, polyvinyl pyrrolidone, fragrances, gel-producing materials, mineral oil, vegetable oil, water, stearyl alcohol, stearic acid, spermaceti, sorbitan monooleate, Polysorbate 80, Tween 60, sorbital solutions, methylcellulose, etc.

Following are specific examples which demonstrate the effectiveness of various forms of this invention.

EXAMPLE I

A number of tests were performed comparing the topical anti-inflammatory activity of theophylline alone or in combination with effective amounts of N-methyl-2-pyrrolidone. The tests were performed on guinea pigs using a known animal inflammation model, namely the guinea pig UV-erythema test. In this test, a large area on the back of each guinea pig used in the test was shaved and depilitated. 18–24 hours after depilitation, each animal received a constant amount of irradiation by fixing the distance from the back of the animal to the light source (11 cm), the area of the surface to be irradiated (2 rings, 2 cm in diameter), the duration of the irradiation (30 seconds) and the intensity of irradiation emitted from the source (360 watt mercury vapor lamp with vycor glass heat filter). (Welhelmi and Domingez, Arch. Internat. Pharmcodyn. 85, 129, 1951).

The weight of the animals was monitored closely and the guinea pigs were randomized before each experiment.

After the exposure to radiation, each guinea pig was painted (using a Q-tip) with about 0.75 ml of the appropriate test solution. The solution was uniformly spread over the entire shaved area. Three or four animals were used for each test solution and/or concentration.

The development of the erythema was recorded at hourly intervals for six hours using a subjective grading system in which each irradiated spot was given a number (0,1,2,3) depending upon the severity of the reaction. The reaction corresponding to each number was defined as follows:

0 — no redness
1 — reddish tint without distinct outline
2 — definite outline of reddish tint
3 — bright red The percent decrease of erythema in drug-treated animals compared to control animals treated with the same composition less the drug was calculated. The results are shown in Table 1.

Table 1.

| | | | % Protection at | | | |
|---|---|---|---|---|---|---|
| | 1 hr | 2 hr | 3 hr | 4 hr | 5 hr | 6 hr |
| A) | | | | | | |
| 70% PEG[1] + 20% N-methyl-2-pyrrolidone + 10% H$_2$O | 0 | 0 | 0 | 0 | 0 | 0 |
| 70% PEG + 9% H$_2$O + 1% theophylline | 0 | 8.0 | 16.7 | 11.0 | 0 | 0 |
| 70% PEG + 1% theophylline + 20% N-methyl-2-pyrrolidone | 100.0 | 100.0 | 87.3 | 55.3 | 44.3 | 33.0 |

Table 1-continued

|  | % Protection at | | | | | |
|---|---|---|---|---|---|---|
|  | 1 hr | 2 hr | 3 hr | 4 hr | 5 hr | 6 hr |
| + 9% H$_2$O | | | | | | |
| B) | | | | | | |
| 20% N-methyl-2-pyrrolidone + 0.01% theophylline + 70% PEG + 9.99% H$_2$O | — | 9.0 | 17.0 | 6.0 | 0 | 0 |
| 20% N-methyl-2-pyrrolidone + 0.1% theophylline + 70% PEG + 9.9% H$_2$O | — | 42.0 | 28.0 | 17.0 | 0 | 0 |
| 20% N-methyl-2-pyrrolidone + 1.0% theophylline + 70% PEG + 9.0% H$_2$O | — | 84.0 | 66.0 | 34.0 | 12.0 | 12.0 |
| 20% N-methyl-2-pyrrolidone + 5.0% theophylline + 70% PEG + 5.0% H$_2$O | — | 0 | 0 | 0 | 0 | 0 |
| C) | | | | | | |
| 20% N-methyl-2-pyrrolidone + 70% PEG + 10% H$_2$O | 0 | 0 | 0 | 0 | 0 | 0 |
| 20% N-methyl-2-pyrrolidone + 70% PEG + 0.1% theophylline + 9.9% H$_2$O | 79.5 | 36.1 | 23.0 | 11.3 | 0 | 0 |
| 20% N-methyl-2-pyrrolidone + 70% PEG + 0.3% theophylline + 9.7% H$_2$O | 100.0 | 72.7 | 70.7 | 55.7 | 44.7 | 27.7 |
| 20% N-methyl-2-pyrrolidone + 70% PEG + 0.7% theophylline + 9.3% H$_2$O | 20.5 | 9.3 | 6.0 | 0 | 0 | 0 |
| 20% N-methyl-2-pyrrolidone + 70% PEG + 1.0% theophylline + 9.0% H$_2$O | 20.5 | 9.3 | 6.0 | 0 | 0 | 0 |
| 20% N-methyl-2-pyrrolidone + 70% PEG + 2.0% theophylline + 8.0% H$_2$O | −20.2 | −9.3 | 0 | 0 | 0 | 0 |
| D) | | | | | | |
| 20% N-methyl-2-pyrrolidone + 70% PEG + 10% H$_2$O | 0 | 0 | 0 | 0 | 0 | 0 |
| 20% N-methyl-2-pyrrolidone + 70% PEG + 0.3% theophylline + 9.7% H$_2$O | 79.5 | 67.0 | 50.0 | 27.7 | 11.3 | 5.7 |

[1] PEG — Polyethylene glycol 300

The results indicate that theophylline in the range of about 0.1 to about 1 percent and preferably about 0.3 percent is an effective anti-inflammatory in the presence of N-methyl-2-pyrrolidone but is ineffective in the absence of N-methyl-2-pyrrolidone.

EXAMPLE II

The following are examples of suitable solution formulations:

|  | Solutions | | |
|---|---|---|---|
|  | A | B | C |
| Theophylline | 0.3% | 0.3% | 0.3% |
| N-methyl-2-pyrrolidone | 10% | 46.6% | 90% |
| Isopropyl myristate | 5% | 5% | 5% |
| Fragrance | 0.1% | 0.1% | 0.1% |
| Adjuvant solvent q.s.ad | Ethanol | Isopropyl alcohol | Acetone |

EXAMPLE III

An aerosol form of formulation B of EXAMPLE 5 is prepared by preparing the following mixture:

| Formulation B | 25% |
|---|---|
| Freon[1] | 75% |

[1] Freon is 75/25 Freon 114/12.

EXAMPLE IV

The following are examples of suitable gel formulations:

|  | Gel | |
|---|---|---|
|  | A | B |
| Theophylline | 0.3% | 0.3% |
| N-methyl-2-pyrrolidone | 96% | 20% |
| Carbopol 934 | 1% | — |
| Carbopol 940 | — | 0.75% |
| Ethanol | — | 50% |
| Ethoxyll 16R | — | 2% |
| Diethanolamine | — | 0.5% |
| di-2(ethylhexyl)amine | 2% | — |
| water q.s.ad | | |

EXAMPLE V

The following are examples of suitable cream formulations:

|  | Creams | | | |
|---|---|---|---|---|
|  | A | B | C | D |
| Theophylline | 0.3% | 0.3% | 0.3% | 0.3% |
| N-methyl-2-pyrrolidone | 25% | 20% | 34% | 42% |
| Stearyl alcohol | 12% | — | — | 10% |
| Stearic acid | — | 19% | 18% | 6% |
| Synthetic spermaceti | 7.5% | — | 2% | 4% |
| Sorbitan monooleate | 1.0% | — | — | — |
| Polysorbate 80 | 5.5% | — | — | — |
| Tween 60 | — | 3.5% | 3.5% | 3.5% |
| Arlacel 60 | — | 1.5% | 3.5% | 1.5% |
| Sorbitol solution | 5.5% | 19.4% | 14% | 10.5% |
| Mineral oil | — | 2.0% | — | — |
| Methocel 90 HG-100 | — | 0.2% | 0.2% | 0.2% |
| Fragrances | 0.2% | — | — | — |
| Sodium citrate | 0.5% | — | — | — |
| Water q.s. ad | | | | |

EXAMPLE VI

Example I is repeated utilizing 2-pyrrolidone, N-ethyl-2-pyrrolidone, N-propyl-2-pyrrolidone and N-butyl-2-pyrrolidone. Comparable results are obtained.

I claim:

1. A composition useful in the treatment of inflammation of the skin comprising about 0.1 to about 1 percent by weight of theophylline together with about 5 to about 99.9 percent by weight of 2-pyrrolidone or N-lower alkyl-2-pyrrolidone.

2. The composition of claim 1 wherein the N-lower alkyl substituent has 1–4 carbon atoms.

3. A composition of claim 1 wherein the N-lower alkyl-2-pyrrolidone is N-methyl-2-pyrrolidone.

4. A composition useful in the treatment of inflammation of the skin comprising about 0.3 theophylline and a topical carrier containing about 10 to about 50 percent by weight N-methyl-2-pyrrolidone.

5. A method for temporarily alleviating the symptoms of inflammation of the skin in humans and animals comprising topically administering to a human or animal an effective amount of a composition containing about 0.1 to about 1 percent by weight of theophylline together with about 5 to about 99.9 percent by weight of 2-pyrrolidone or an N-lower alkyl-2-pyrrolidone.

6. The method of claim 5 wherein the N-lower alkyl substituent has 1–4 carbon atoms.

7. The method of claim 5 wherein the N-lower alkyl-2-pyrrolidone is N-methyl-2-pyrrolidone.

8. A method for temporarily alleviating the symptoms of inflammation of the skin in humans and animals comprising topically administering to a human or animal an effective amount of a composition containing about 0.3 percent by weight of theophylline and a topical carrier containing about 10 to about 50 percent by weight of N-methyl-2-pyrrolidone.

9. The method of claim 5 wherein the inflammation is sunburn.

10. The method of claim 8 wherein the inflammation is sunburn.

* * * * *

UNITED STATES PATENT OFFICE
CERTIFICATE OF CORRECTION

PATENT NO. : 3,957,994
DATED : May 18, 1976
INVENTOR(S) : Richard Allen Schroer

It is certified that error appears in the above-identified patent and that said Letters Patent are hereby corrected as shown below:

Table 1

A) reads: 70% PEG + 9% $H_2O$ + 1% theophylline should read

- 70% PEG + 29% $H_2O$ + 1% theophylline -

Signed and Sealed this

Ninth Day of November 1976

[SEAL]

Attest:

RUTH C. MASON
Attesting Officer

C. MARSHALL DANN
Commissioner of Patents and Trademarks